United States Patent [19]

Gregory et al.

[11] Patent Number: 4,942,183

[45] Date of Patent: Jul. 17, 1990

[54] AMINOMETHYL OXOOXAZOLIDINYL AROYLBENZENE DERIVATIVES USEFUL AS ANTIBACTERIAL AGENTS

[75] Inventors: Walter A. Gregory; Hollis S. Kezar, III, both of Wilmington, Del.

[73] Assignee: E. I. Du Pont de Nemours and Company, Wilmington, Del.

[21] Appl. No.: 376,456

[22] Filed: Jul. 7, 1989

Related U.S. Application Data

[63] Continuation of Ser. No. 109,032, Oct. 16, 1987, abandoned.

[51] Int. Cl.$^5$ .................... A61K 31/42; C07D 263/22
[52] U.S. Cl. ...................... 514/376; 514/252; 514/340; 544/360; 544/369; 546/275; 546/276
[58] Field of Search ............ 548/228, 232, 234; 514/376; 546/275

[56] References Cited

U.S. PATENT DOCUMENTS

| | | | |
|---|---|---|---|
| Re. 29,607 | 4/1978 | Fauran et al. | 548/229 |
| 3,687,965 | 8/1972 | Fauran et al. | 548/229 |
| 4,128,654 | 12/1978 | Fugitt et al. | 514/376 |
| 4,250,318 | 2/1981 | Dostert et al. | 548/229 |
| 4,340,606 | 7/1982 | Fugitt et al. | 514/376 |
| 4,461,773 | 7/1984 | Gregory | 514/376 |
| 4,476,136 | 10/1984 | Dostert et al. | 548/229 |
| 4,705,799 | 11/1987 | Gregory et al. | 548/229 |
| 4,801,600 | 1/1989 | Wang et alk. | 548/234 |

FOREIGN PATENT DOCUMENTS

0127902 12/1984 European Pat. Off. .
0184170 6/1986 European Pat. Off. .
2094299 9/1982 United Kingdom .

OTHER PUBLICATIONS

Burger, A. Guide to the Chemical Basis of Drug Design (1983: Wiley Interscience, New York) p. 15.

*Primary Examiner*—Donald G. Daus
*Attorney, Agent, or Firm*—Robert W. Black; Gildo E. Fato

[57] ABSTRACT

Aminomethyl oxooxazolidinyl aroylbenzene derivatives, such as l-N-[3-[4-(2,4-difluorobenzoyl)phenyl]-2-oxooxazolidin-5-ylmethyl]acetamide, possess useful antibacterial activity.

36 Claims, No Drawings

AMINOMETHYL OXOOXAZOLIDINYL AROYLBENZENE DERIVATIVES USEFUL AS ANTIBACTERIAL AGENTS

This application is a continuation of application Ser. No. 109,032, filed Oct. 16, 1987.

TECHNICAL FIELD

This invention relates to novel aminomethyl oxooxazolidinyl aroylbenzene derivatives, their preparation, to pharmaceutical compositions containing them, and to methods of using them to alleviate bacterial infections.

BACKGROUND OF THE INVENTION

At the present time, no existing antibacterial product provides all features deemed advantageous. There is continual development of resistance by bacterial strains. A reduction of allergic reactions and of irritation at the site of injection, and greater biological half-life (i.e., longer in vivo activity) are currently desirable features for antibacterial products.

U.S. Pat. No. 4,128,654 issued to Fugitt et al. on Dec. 5, 1978, discloses, among others, compounds of the formula:

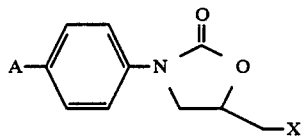

where
A=RS(O)$_n$;
X=Cl, Br or F;
R=C$_1$-C$_3$ alkyl; and
n=0, 1 or 2.

The compounds are disclosed as being useful in controlling fungal and bacterial diseases of plants.

U.S. Reissue Pat. No. 29,607 reissued Apr. 11, 1978 discloses derivatives of 5-hydroxymethyl-3-substituted-2-oxazolidinones of the formula:

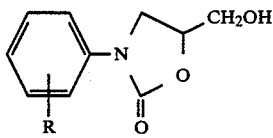

where R is H, F, CH$_3$, or CF$_3$. Such compounds are described as having antidepressive, tranquilizing, sedative, and antiinflammatory properties.

U.S. Pat. No. 4,250,318, which was issued on Feb. 10, 1981, discloses antidepressant compounds of the formula:

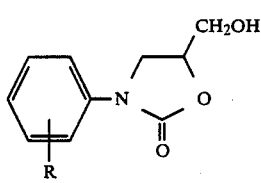

where R can be, among others, a para-n-pentylamino group, an SR$_1$ group where R$_1$ is C$_1$-C$_5$ alkyl, or an acetylmethylthio group.

U.S. Pat. No. 4,340,606 issued to Fugitt et al. on Jul. 20, 1982, discloses antibacterial agents of the general formula:

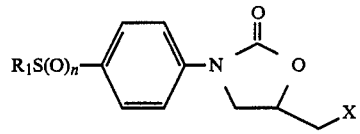

where
R$_1$=CH$_3$, C$_2$H$_5$, CF$_2$H, CF$_3$ or CF$_2$CF$_2$H; and
X=OR$_2$ (R$_2$=H or various acyl moieties).

U.S. Pat. No. 3,687,965, issued to Fauran et al. on Aug. 29, 1972, discloses compounds of the formula:

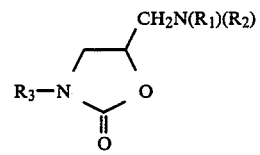

where
—N(R$_1$)(R$_2$) represents either dialkylamino radical in which the alkyl portions have one to five carbon atoms, or a heterocyclic amino radical which may be substituted by an alkyl radical having one to five carbon atoms or by a pyrrolidinocarbonylmethyl radical, and R$_3$ represents a phenyl radical which may be substituted by one or more of the following radicals:
an alkoxy radical having one to five carbon atoms;
a halogen atom;
a trifluoromethyl radical, or
a carboxyl radical which may be esterified.

The patent states that these compounds possess hypotensive, vasodilatatory, spasmolytic, sedative, myorelaxant, analgesic and antiinflammatory properties. There is no mention of antibacterial properties.

Belgian Patent 892,270, published Aug. 25, 1982, discloses monoamine oxidase inhibitors of the formula

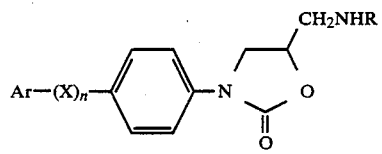

where
R is H, C$_1$-C$_4$ alkyl or propargyl;
Ar is phenyl, optionally substituted by halo or trifluoromethyl;
n is 0 or 1; and
X is —CH$_2$CH$_2$—, —CH=CH—, an acetylene group or —CH$_2$O—.

U.S. Pat. No. 4,461,773 issued to W. A. Gregory on Jul. 24, 1984, discloses antibacterial agents of the formula

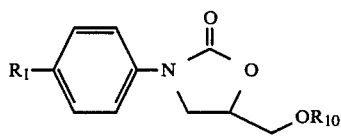

wherein, for the l, and mixtures of the d and l stereoisomers of the compound,
$R_1$ is $R_2SO_2$,

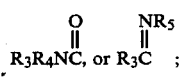

$R_2$ or —NR$_3$R$_4$, —N(OR$_3$)R$_4$, —N$_3$, —NHNH$_2$, —NX$_2$, —NR$_6$X, —NXZ,

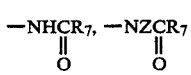

or —N=S(O)$_n$R$_8$R$_9$;
$R_3$ and $R_4$ are independently H, alkyl of 1–4 carbons or cycloalkyl of 3–8 carbons;
$R_5$ is NR$_3$R$_4$ or OR$_3$;
$R_6$ is alkyl of 1–4 carbons;
$R_7$ is alkyl of 1–4 carbons, optionally substituted with one or more halogens;
$R_8$ and $R_9$ are independently alkyl of 1–4 carbons or, taken together are —(CH$_2$)$_p$—;
$R_{10}$ is H, alkyl of 1–3 carbons,

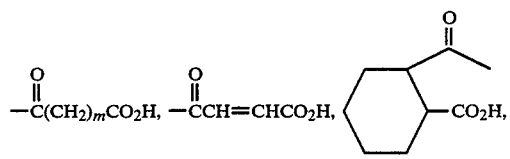

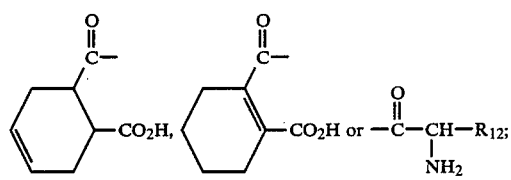

$R_{11}$ is alkyl of 1–12 carbons;
$R_{12}$ is H, alkyl of 1–5 carbons, CH$_2$OH or CH$_2$SH;
X is Cl, Br or I;
Z is a physiologically acceptable cation;
m is 2 or 3;
n is 0 or 1; and
p is 3, 4 or 5;
and when $R_{10}$ is alkyl of 1–3 carbons, $R_1$ can also be CH$_3$S(O)$_q$ where q is 0, 1 or 2;
or a pharmaceutically acceptable salt thereof.

European Patent Application 127,902, published Dec. 12, 1984, and 184,170, published Jun. 11, 1986, disclose antibacterial agents of the formula:

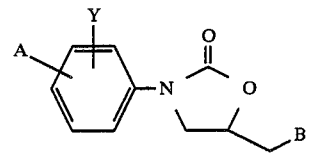

wherein, for the l, and mixtures of the d and l stereoisomers of the compound,
A is —NO$_2$, —S(O)$_n$R$_1$, —S(O)$_2$—N=S(O)$_p$R$_2$R$_3$, —SH,

—COR$_{23}$, —COR$_{25}$, —CONR$_5$R$_6$,

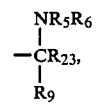 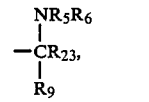

CN, —OR$_5$ halogen, —NR$_5$R$_6$,

—NCOR$_4$, NS(O)$_n$R$_4$,

CR$_{23}$(OR$_{16}$)OR$_{17}$,

alkyl of 1 to 8 carbons, optionally substituted with one or more halogen atoms, OH, =O other than at alpha position, S(O)$_n$R$_{24}$, NR$_5$R$_6$, alkenyl of 2–5 carbons, alkynyl of 2–5 carbons or cycloalkyl of 3–8 carbons;
$R_1$ is C$_1$–C$_4$ alkyl, optionally substituted with one or more halogen atoms, OH, CN, NR$_5$R$_6$ or CO$_2$R$_8$; C$_2$–C$_4$ alkenyl; —NR$_9$R$_{10}$; —N$_3$;

—NHCR$_4$ —NZCR$_4$;

—NX$_2$; —NR$_9$X; —NXZ$^+$;
$R_2$ and $R_3$ are independently C$_1$–C$_2$ alkyl or, taken together are —(CH$_2$)$_q$—;
$R_4$ is alkyl of 1–4 carbons, optionally substituted with one or more halogens;
$R_5$ and $R_6$ are independently H, alkyl of 1–4 carbons or cycloalkyl of 3–8 carbons;
$R_7$ is —NR$_5$R$_6$, —OR$_5$ or

NHCR$_5$;

$R_8$ is H or alkyl of 1–4 carbons;
$R_9$ is H, C$_1$–C$_4$ alkyl or C$_3$–C$_8$ cycloalkyl;
$R_{10}$ is H, C$_1$–C$_4$ alkyl, C$_2$–C$_4$ alkenyl, C$_3$–C$_4$ cycloalkyl, —OR$_8$ or —NR$_{11}$R$_{11A}$;

$R_{11}$ and $R_{11A}$ are independently H or $C_1$-$C_4$ alkyl, or taken together, are —$(CH_2)_r$—;

X is Cl, Br or I;

Y is H, F, Cl, Br, alkyl or 1-3 carbons, or $NO_2$, or A and Y taken together can be —O—$(CH_2)_tO$—;

Z is a physiologically acceptable cation;

n is 0, 1 or 2;

p is 0 or 1;

q is 3, 4 or 5;

r is 4 or 5;

t is 1, 2 or 3;

B is —$NH_2$, $$-\underset{\underset{R_{12}}{|}}{N}-\underset{\underset{}{\overset{O}{\|}}}{C}-R_{13}, \quad -\underset{\underset{R_{12}}{|}}{N}-S(O)_uR_{14},$$

or $N_3$;

$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; —$CH_2OR_{15}$; —$CH(OR_{16})OR_{17}$; —$CH_2S(O)_vR_{14}$;

$$\overset{O}{\underset{}{\|}}\\ CR_{15};$$

—$OR_{18}$; —$SR_{14}$; —$CH_2N_3$; the aminoalkyl groups derived from α-amino acids such as glycine, L-alanine, L-cysteine, L-proline, and D-alanine; —$NR_{19}R_{20}$; or $C(NH_2)R_{21}R_{22}$;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —$(CH_2)_m$—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —$(CH_2)_s$—;

u is 1 or 2;

v is 0, 1 or 2;

m is 2 or 3;

s is 2, 3, 4 or 5; and $R_{23}$ is H, alkyl of 1-8 carbons optionally substituted with one or more halogens, or cycloalkyl of 3-8 carbons;

$R_{24}$ is alkyl of 1-4 carbons or cycloalkyl of 3-8 carbons;

$R_{25}$ is alkyl of 1-4 carbons substituted with one or more of —$S(O)_nR_{24}$, —$OR_8$, $$\overset{O}{\underset{}{\|}}\\ -OCR_8,$$

—$NR_5R_6$, or alkenyl of 2-5 carbons optionally substituted with CHO; or a pharmaceutically suitable salt thereof; provided that:

(1) when A is $CH_3S$—, then B is not $$-\underset{\underset{CH_3}{|}}{N}-CO_2CH_3;$$

(2) when A is $CH_3SO_2$—, then B is not $$-\underset{\underset{CH_3}{|}}{N}-COCH_3 \text{ or } -\underset{\underset{CH_3}{|}}{N}-COCF_3;$$

(3) when A is $H_2NSO_2$— and B is $$-\underset{\underset{R_{12}}{|}}{N}-\overset{O}{\underset{}{\|}}CR_{13},$$

then (4) when A is —CN, B is not —$N_3$;

(5) when A is $(CH_3)_2CH$, B is not $NHCOCH_2Cl$;

(6) when A is $OR_5$, then B is not $NH_2$;

(7) when A is F, then B is not $NHCO_2CH_3$.

None of the above-mentioned references suggest the novel antibacterial compounds of this invention.

SUMMARY OF THE INVENTION

According to the present invention, there is provided an oxazolidinone having the formula:

wherein for the l isomer or racemic mixtures containing it

B is $NH_2$, $$-\underset{\underset{R_3}{|}}{N}-\overset{O}{\underset{}{\|}}C-R_4, \quad -\underset{\underset{R_3}{|}}{N}-S(O)_uR_5,$$

or $N_3$ u is 1 or 2;

$R_3$ is H, alkyl of 1-10 carbon atoms, or cycloalkyl of 3-8 carbon atoms;

$R_4$ is H, alkyl of 1-4 carbon atoms, alkenyl of 2-4 carbon atoms, cycloalkyl of 3-4 carbon atoms, or $OR_5$;

$R_5$ is alkyl of 1-4 carbon atoms;

$R_1$ and $R_2$ taken together are $H_2$, H and OH, =O, =NOH, H and $N(R_6)_2$, =$NOR_5$, $$=NOCR_4 \text{ or } =N-N\underset{\underset{}{}}{\overset{}{\diagup\!\!\!\diagdown}}N-CH_3;$$

$R_6$ is H or alkyl of 1-4 carbon atoms;

X is pyridinyl or phenyl optionally substituted with from 1-3 substituents each independently selected from a group selected from halogen, alkyl of 1-4 carbon atoms, $NO_2$, $OR_5$, or $S(O)_mR_5$; and m is 0, 1 or 2;

or a pharmaceutically suitable salt thereof.

Also provided is a process for preparing compounds of Formula (I), such a process being described in detail hereinafter.

Additionally provided are a pharmaceutical composition containing a compound of Formula (I) and a method of using a compound of Formula (I) to treat a bacterial infection in a mammal.

PREFERRED EMBODIMENTS

Preferred compounds are the oxazolidinones of Formula (I) wherein:

(a) B is $$-NHCR_4;$$
$$\quad\;\; \|$$
$$\quad\;\; O$$

where $R_4$ is H, $CH_3$, or $OR_5$; or (b) $R_1$ and $R_2$ taken together are $H_2$, H and OH, =O, =NOH, or

=N—N  N—CH$_3$;

or (c) X is 3-pyridinyl or phenyl optionally substituted with from 1-2 substituents each independently selected from halogen, $NO_2$, $S(O)_m R_5$ or $OR_5$.

More preferred compounds are the oxazolidinones of Formula (I) wherein:

(a) B is $$-NHCCH_3;$$
$$\quad\;\; \|$$
$$\quad\;\; O$$

or (b) $R_1$ and $R_2$ taken together are $H_2$, H and OH, =O, or

=N—N  N—CH$_3$;

or (c) X is phenyl optionally substituted with from 1-2 substituents each selected from F, Cl, $NO_2$, or $OCH_3$.

Specifically preferred are the following compounds:
(l)-N-[3-[4-(2,4-difluorobenzoyl)phenyl]-2-oxooxazolidin-5-ylmethyl]acetamide;
(l)-N-[3-[4-(4-nitrobenzoyl)phenyl]-2-oxooxazolidin-5-ylmethyl]acetamide;
(l)-N-[3-[4-(4-fluorobenzoyl)phenyl]-2-oxooxazolidin-5-ylmethyl]acetamide.

DETAILED DESCRIPTION

The compounds of Formula (I) contain at least one chiral center and, as such, exist as two individual isomers or as a mixture of both. This invention relates to the levorotatory isomer (l), which for many of the compounds in this invention can be referred to as the (S) isomer, as well as mixtures containing both the (R) and (S) isomers. Additional chiral centers may be present in the B group, or when $R_1$ and $R_2$ taken together are H and OH or H and $N(R_6)_2$. The invention relates to all possible stereoisomers of the above.

For the purposes of this invention, the l-isomer of compounds of Formula (I) is intended to mean compounds of the configuration depicted; when B is NHAc, and closely related groups, this isomer is described as the (S) isomer in the Cahn-Ingold-Prelog nomenclature:

Synthesis

Compounds of Formula (I) where $R_1$ and $R_2$ taken together are =O, and X and B are as previously defined can be prepared as follows:

Scheme 1

Compounds of Formula (II), which are prepared by the process previously described in published European applications 127,902 and 184,170, are converted to aroyl derivatives (III) by treatment of either a mixture of methanesulfonic acid and methanesulfonic anhydride or a mixture of trifluoromethanesulfonic acid and trifluoromethanesulfonic anhydride and the corresponding aroyl carboxylic acid at room temperature to 80° C.

Compounds of Formula (I) where $R_1$ and $R_2$ taken together are not =O but as described previously can be prepared as follows:

Scheme 2

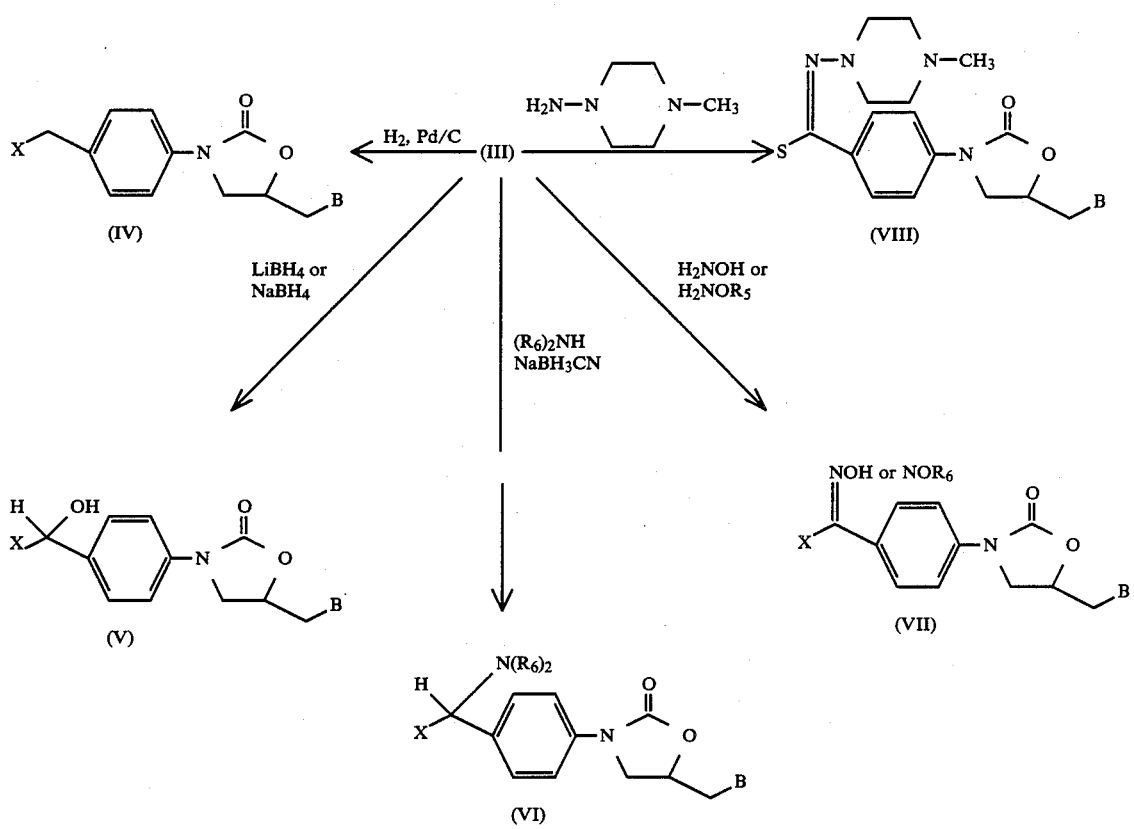

Aroyl derivatives (III) can be converted to compounds (IV)–(VIII) by standard procedures. Hydrogenation of (III) in a solvent such as ethyl acetate, methanol, or ethanol in the presence of a hydrogenation catalyst such as Pd/C or Pt/C under 0–15 lb hydrogen pressure at room temperature to 80° C. gives (IV). Alcohols (V) are prepared according to the procedure described in Example 19 by use of an alkali metal borohydride. Reaction of (III) with $(R_6)_2NH$ in an alcoholic solvent such as methanol or ethanol at room temperature to 80° C. in the presence of sodium cyanoborohydride affords amines (VI). Treatment of (III) with hydroxyamine hydrochloride or $H_2NOR_5$ in the presence of a base such as pyridine or triethylamine in an alcoholic solvent such as methanol or ethanol at room temperature to 100° C. yields oximes (VII). Finally, aroyl derivatives (III) are converted to (VIII) by reacting with 1-amino-4-methylpiperazine in a refluxing solvent such as tetrahydrofuran (THF) or dioxane containing boron trifluoride etherate.

Pharmaceutically suitable salts of compounds of Formula (I) can be prepared in a number of ways known in the art. When $R_1$, $R_2$, X or B contain a basic nitrogen, pharmaceutically salts include these resulting from treatment with acids such as acetic, hydrochloric, sulfuric, phosphoric, succinic, fumaric, ascorbic and glutaric acid.

The invention can be further understood by the following examples in which parts and percentages are by weight unless indicated otherwise.

EXAMPLE 1

Preparation of (l)-N-[3-[4-(4-fluorobenzoyl)phenyl]-2-oxooxazolidin-5-ylmethyl]acetamide (I; $R_1$, $R_2$=O, X=4-$C_6H_4F$, B=NHCOCH$_3$)

To a solution of methanesulfonic anhydride (7.45 g, 43 mmol), methanesulfonic acid (14 mL), and (l)-N-(3-phenyl-2-oxo-5-oxazolidin-5-yl-methyl)acetamide (2.0 g, 9 mmol) was added 4-fluorobenzoic acid (4.8 g, 34 mmol). The mixture was stirred at 50°–60° C. overnight and allowed to cool to room temperature before being poured into 120 mL ice/water. The resulting mixture was extracted with a chloroform/2-propanol mixture. The organic extract was washed with saturated sodium bicarbonate, saturated brine and dried ($Na_2SO_4$). The solvent was removed in vacuo and the residue was purified by flash chromatography followed by crystallization from ethyl acetate. Recovered 2.2 g (73%) of the title compound, m.p. 168.5°–170.5° C. IR (KBr): 1752, 1652, 1600 cm$^{-1}$; NMR (d$_6$-DMSO) δ:8.29 (m,1H), 7.78 (m,6H), 7.40 (m,2H), 4.79 (m,1H), 4.20 (dd,J=9,9 Hz,1H), 3.83 (dd,J=6.5, 9.1 Hz,1H), 3.45 (m,2H), 1.83 (s,3H); C,H analysis, calcd: C 64.04, H 4.81, F 5.33, N 7.86, found: C 64.12, H 4.82, F 5.37, N 7.90; $[\alpha]_D$=−31° (c=1.01, acetone).

By using the procedure described in Example 1, the following compounds in Table I were prepared or can be prepared.

TABLE I

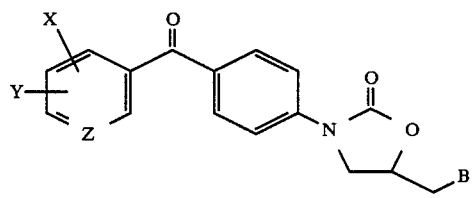

| Ex. | X | Y | Z | B | Isomer | m.p. (°C.) |
|---|---|---|---|---|---|---|
| 1 | 4-F | H | CH | NHCOCH₃ | l | 168.5–170.5 |
| 2 | H | H | CH | NHCOCH₃ | l | 175–177 |
| 3 | 4-OCH₃ | H | CH | NHCOCH₃ | l | 162–163.5 |
| 4 | 4-Cl | H | CH | NHCOCH₃ | l | 222.5–224 |
| 5 | 3-F | H | CH | NHCOCH₃ | l | 166.5–168 |
| 6 | 2-F | 4-F | CH | NHCOCH₃ | l | 169–170 |
| 7 | 2-OCH₃ | 4-Cl | CH | NHCOCH₃ | l | 212–214 |
| 8 | 4-SCH₃ | H | CH | NHCOCH₃ | l | |
| 9 | 4-NO₂ | H | CH | NHCOCH₃ | l | 220–222 |
| 10 | 4-SOCH₃ | H | CH | NHCOCH₃ | l | |
| 11 | 4-SO₂CH₃ | H | CH | NHCOCH₃ | l | |
| 12 | H | H | CH | NH₂ | l | |
| 13 | H | H | CH | N₃ | l | |
| 14 | H | H | CH | NHCO—◁ | dl | |
| 15 | H | H | N | NHCOCH₃ | l | 184–185.5 |
| 16 | 4-CH₃ | H | CH | NHSOC₂H₅ | dl | |
| 17 | 2-C₂H₅ | H | CH | N(CH₃)SO₂CH₃ | l | |
| 18 | H | H | N | N(C₂H₅)COCH₃ | l | |

EXAMPLE 19

Preparation of
(l)-N-[3-[4-[(4-fluorophenyl)(hydroxy)methyl]phenyl]-2-oxooxazolidin-5-ylmethyl]acetamide (I; $R_1$=H, $R_2$=OH, X=4-$C_6H_4F$, B=NHCOCH₃)

To a solution of (l)-N-[3-[4-[(4-fluorobenzo)phenyl]-2-oxooxazolidin-5-ylmethyl]acetamide (1.50 g, 4.2 mmol) in THF (30 mL) was added lithium borohydride (1.05 mL, 2M in THF, 2.1 mmol). The mixture was stirred at room temperature overnight before quenching with water followed by 1N hydrochloric acid. The solution was diluted with 1N hydrochloric acid and extracted with a chloroform/2-propanol mixture. The organic extract was washed with saturated sodium bicarbonate, saturated brine and dried ($Na_2SO_4$). The solvent was removed in vacuo and the residue was purified by flash chromatography. Recovered 0.52 g (34%) of the title compound, m.p. 73°–76° C. IR (KBr): 1745,1655 cm⁻¹; NMR (d₆-DMSO) δ:8.24 (m,1H), 7.41 (m,6H), 7.10 (m,2H), 5.93 (d,J=4 Hz,1H), 5.70 (d,J=4 Hz,1H), 4.69 (m,1H), 4.06 (m,1H), 3.71 (m,1H), 3.39 (m,1H), 1.83 (s,3H); MS: m/z 358.1335 (m+), calcd. for $C_{19}H_{19}N_2O_4F$, 358.1329; [α]$_D$=−12° (C=1.0, ethanol).

By using the procedure described in Example 19, the following compounds in Table II were prepared or can be prepared.

TABLE II

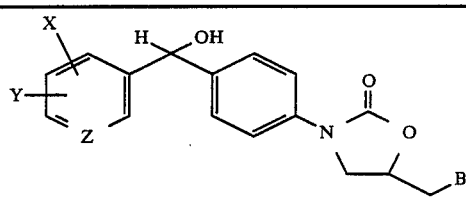

| Ex. | X | Y | Z | B | Isomer | m.p. (°C.) |
|---|---|---|---|---|---|---|
| 19 | 4-F | H | CH | NHCOCH₃ | l | 73–76 |
| 20 | H | H | CH | NHCOCH₃ | l | 68–70 |
| 21 | 2-F | 4-F | CH | NHCOCH₃ | l | 70–73 |
| 22 | 4-SCH₃ | H | CH | NHCOCH₃ | l | |
| 23 | H | H | CH | NHCO₂CH₃ | dl | |
| 24 | 4-CH₃ | H | CH | NHSOCH₃ | l | |
| 25 | 2-C₂H₅ | H | CH | NHSO₂C₄H₉ | l | |
| 26 | H | H | N | NHCOCH₃ | l | |
| 27 | 4-F | H | CH | N₃ | dl | |
| 28 | H | H | CH | NH₂ | l | |
| 29 | H | H | CH | N(CH₃)COC₂H₅ | dl | |

By using chemistry previously described in Synthesis section, compounds in Table III can be prepared.

TABLE III

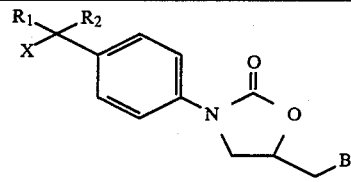

| Ex. | X | $R_1, R_2$ | B | Isomer | m.p. (°C.) |
|---|---|---|---|---|---|
| 30 | $C_6H_5$ | =N—N⟨piperazine⟩N—$CH_3$ | $NHCOCH_3$ | l | |
| 31 | $4-FC_6H_4$ | $H, NH_2$ | $NHSOCH_3$ | dl | |
| 32 | $4-ClC_6H_4$ | $H, N(CH_3)_2$ | $N_3$ | l | |
| 33 | $2,4-F_2C_6H_4$ | =NOH | $NH_2$ | l | |
| 34 | $4-CH_3C_6H_4$ | =$NOCH_3$ | $NHCO_2CH_3$ | dl | |
| 35 | 2-pyridyl | =$NOCC_2H_5$ (O=) | NHCO—⟨cyclopropyl⟩ | l | |
| 36 | 3-pyridyl | $H, NH_2$ | $N(CH_3)COC_2H_5$ | l | |
| 37 | 4-pyridyl | =N—N⟨piperazine⟩N—$CH_3$ | $N(C_2H_5)SO_2CH_3$ | l | |

Dosage Forms

The antibacterial agents of this invention can be administered by any means that produces contact of the active agent with the agents' site of action in the body of a mammal. They can be administered by any conventional means available for use in conjunction with pharmaceuticals, either as individual therapeutic agents or in a combination of therapeutic agents. They can be administered alone, but are generally adminsitered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually, a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided oral doses 2 to 4 times a day or in sustained release form, is effective to obtain desired results. These drugs may also be administered parenterally.

Projected therapeutic levels in humans should be attained by the oral administration of 5–20 mg/kg of body weight given in divided doses two to four times daily. The dosages may be increased in severe or life-threatening infections.

Dosage forms (compositions) suitable for internal administration contain from about 0.1 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, manitol, starch, cellulose derivatives, magnesium stearate, steric acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances. Antioxidants such as sodium bisufate, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capusles containing 75 milligrams of the active ingredient. The capusles was washed and dried.

Tablets

A large number of tablets are prepared by conventional procedures so that the dosage unit is 75 milligrams of active ingredient, 0.2 milligrams of colloidal silicon dioxide, 5 milligrams of magnesium stearate, 250 milligrams for microcrystalline cellulose, 11 milligrams of cornstarch and 98.8 milligrams of lactose. Appropriate coatings may be applied to increase palatability or delay absorption.

Injectables

A parenteral composition suitable for administration by injection is prepared by stirring 1.5% by weight of active ingredient in 10% by volume propylene glycol and water. The solution is made isotonic with sodium chloride and sterilized.

Suspensions

An aqueous suspension is prepared for oral administration os that each 5 milliliters contain 75 milligrams of finely-divided active ingredients. 200 milligrams of sodium carboxymethyl cellulose, 5 milligrams of solium benzoate, 1.0 grams of sorbitol solution, U.S. P., and 0.025 milliliters of vanillin.

Cl Utility

Test results indicate that the novel compounds of this invention are biologically active against gram positive bacteria including multiply antibiotic resistant strains of staphylococci and streptococci. These compounds are potentially useful for the treatment of both human and animal bacterial infections including diseases of the respiratory, gastrointestinal, genitourinary systems; blood; interstitial fluids; and soft tissues.

As shown in Table IV, compounds of Formula (I) exert an in vitro antibacterial effect. A standard microdilution method (*National Committee for Clinical Standards. Tentative standard M7-T.* Standard methods for dilution antimicrobial susceptibility tests for bacteria that grow aerobically. National Committee for Clinical Laboratory Standards, Villanova, Pa. 1982) with Mueller-Hinton broth is used to determine the 24-hour minimal inhibitory concentrations (MIC's) for test strains of *Staphylococcus aureus* and *Escherichia Coli.*

The in vivo potency of these compounds is exemplified by the data summarized in Table V. Determinations of in vivo efficacy are performed by inoculating mice intraperitoneally with cultures of the infecting organism diluted to produce 100% mortality in control animals within twenty-four hours. The culture of S. aureus used to infect the animals was diluted to the required baceterial density using 5% aqueous hog gastric mucin. The compounds are dissolved or suspended in 0.25% aqueous Methocel ® (Methocel ®; Hydroxypropyl Methylcellulose, E15 Premium, Dow Chemical Company) for oral administration or sterile distilled water containing 5% dimethylsulfoxide (Fisher Scientific Compnay, Fairlawn, N.J.) for subcutaneous administration. The mice are dosed at one hour and at four hours post-infection. Mortality is recorded daily until test termination seven days post infection. The number of survivors in each treatment group on the seventh day after infection is used in the calculation of the $ED_{50}$, the dose of compound that protects 50% of the mice (Litchfield, J. T. and Wildoxon. A simplified method for evaluating dose-effect experiments. *J. Pharmacol Exp. Ther.*, 96:99–113, 1949).

TABLE IV

In Vitro Broth Microdilution Minimal Inhibitory Concentrations (MIC's)

| Ex. No. | Minimum Inhibitory Concentration ($\mu g/mL$) | |
| --- | --- | --- |
|  | *Staphylococcus aureus* | *Escherichia coli* |
| 1 | 4 | >128 |
| 2 | 4 | >128 |
| 3 | 4 | >128 |
| 5 | 8 | >128 |
| 6 | 1 | >128 |
| 7 | 32 | >128 |
| 8 | 4 | >128 |
| 9 | 1 | >128 |
| 10 | 16 | >128 |
| 11 | 4 | >128 |
| 15 | 8 | >128 |
| 20 | 32 | >128 |

TABLE V

In Vivo Activity of Compounds Against *Staphylococcus Aureus* in an Acute Lethal Mouse Model

| Ex. No. | $ED_{50}$ (mg/kg) | |
| --- | --- | --- |
|  | Oral Administration | Subcutaneous Administration |
| 1 | 40 | 20 |
| 2 | 47 | 60 |
| 3 | 41 | 15 |
| 5 | 42 | 25 |
| 6 | 30 | 26 |
| 7 | >120 | >120 |
| 8 | >90 | >90 |
| 9 | >90 | >90 |
| 10 | >90 | >90 |
| 11 | >90 | >90 |
| 15 | >90 | 59 |
| 20 | 65 | 52 |

What is claimed is:

1. A compound having the formula:

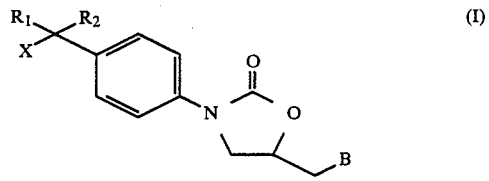

wherein for the l isomer or racemic mixtures containing it

B is $NH_2$,

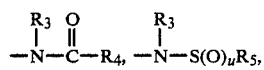

or N₃ u is 1 or 2;

R₃ is H, alkyl of 1-10 carbon atoms, or cycloalkyl of 3-8 carbon atoms;

R₄ is H, alkyl of 1-4 carbon atoms, alkenyl of 2-4 carbon atoms, cycloalkyl of 3-4 carbon atoms, or OR₅;

R₅ is alkyl of 1-4 carbon atoms;

R₁ and R₂ taken together are H₂, H and OH, =O, =NOH, H and N(R₆)₂, =NOR₅, or

is H or alkyl of 1-4 carbon atoms;

X is pyridinyl or phenyl optionally substituted from 1-3 substituents each independently selected from a group selected from halogen, alkyl of 1-4 carbon atoms, OR₅, or S(O)ₘR₅; provided that when X is S(O)ₘR₅, it comprises only 1 substituent; and m is 0, 1 or 2;

or a pharmaceutically suitable salt thereof.

2. A compound of claim 1 wherein B is

where R₄ is H, CH₃, or OR₅.

3. A compound of claim 1 wherein R₁ and R₂ taken together are H₂, H and OH, =O, or =NOH.

4. A compound of claim 1 wherein X is 3-pyridinyl or phenyl optionally substituted with 1-2 substituents each independently selected from halogen, S(O)ₘR₅, or OR₅.

5. A compound of claim 1 wherein:

(a) B is

where R₄ is H, CH₃, or OR₅;

(b) R₁ and R₂ taken together are H₂, H and OH, =O, or =NOH; and (c) X is 3-pyridinyl or phenyl optionally substituted with 1-2 substituents each independently selected from halogen, S(O)ₘR₅, or OR₅ provided that when X is S(O)ₘR₅, it comprises only 1 substituent.

6. A compound of claim 1 wherein B is

7. A compound of claim 1 wherein R₁ and R₂ taken together are H₂, H and Oh, or =O.

8. A compound of claim 1 wherein X is phenyl optionally substituted with from 1-2 substituents each selected from F, Cl, or OCH₃.

9. A compound of claim 1 wherein:

(a) B is

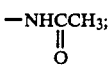

(b) R₁ and R₂ taken together are H₂, H and OH, or =O;

(c) X is phenyl optioally substituted with from 1-2 substituents each selected from F, Cl, or OCH₃.

10. The compound of claim 1 which is (l)-N-[3-[4-(2,4-difluorobenzoyl)phenyl]-2-oxo-oxazolidin-5-ylmethyl]acetamide.

11. The compound of claim 1 which is (l)-N-[3-[4-(4-nitrobenzoyl)phenyl]-phenyl]-2-oxooxazo-lidin-5-ylmethyl]acetamide.

12. The compound of claim 1 which is (l)-N-[3-[4-(4-fluorobenzoyyl)phenyl]-]-2-oxooxazo-lidin-5-ylmethyl]acetamide.

13. A pharmaceutical composition consisting essentially of a pharmaceutically suitable carrier and an antibacterial amount of a compound of claim 1.

14. A pharmaceutical composition consisting essentially of a pharmaceutically suitable carrier and an antibactrial amount of a compound of claim 2.

15. A pharmaceutical composition consisting essentially of a pharmaceutically suitable carrier and an antibacterial amount of a compound of claim 3.

16. A pharmaceutical composition consisting essentially of a pharmaceutically suitable carrier and an antibacterial amount of a compound of claim 4.

17. A pharmaceutical composition consisting essentially of a pharmaceutically suitable carrier and an antibacterial amount of a compound of claim 5.

18. A pharmaceutical composition consisting essentially of a pharmaceutically suitable carrier and an antibacterial amount of a compound of claim 6.

19. A pharmaceutical composition consisting essentially of a pharmaceutically suitable carrier and an antibacterial amount of a compound of claim 7.

20. A pharmaceutical composition consisting essentially of a pharmaceutically suitable carrier and an antibacterial amount of a compound of claim 8.

21. A pharmaceutical composition consisting essentially of a pharmaceutically suitable carrier and an antibacterial amount of a compound of claim 9.

22. A pharmaceutical composition consisting essentially of a pharmaceutically suitable carrier and an antibacterial amount of the compound of claim 10.

23. A pharmaceutical composition consisting essentially of a pharmaceutically suitable carrier and an antibacterial amount of the compound of claim 11.

24. A pharmaceutical composition consisting essentially of a pharmaceutically suitable carrier and an antibacterial amount of the compound of claim 12.

25. A method treating a bacterial infection in a mammal comprising administering to the mammal an antibacterial amount of a compound of claim 1.

26. A method of treating a bacterial infection in a mammal comprising administering to the mammal an antibacterial amount of a compound of claim 2.

27. A method of treating a bacterial infection in a mammal comprising administering to the mammal an antibacterial amount of a compound of claim 3.

28. A method of treating a bacterial infection in a mammal comprising administering to the mammal an antibacterial amount of a compound of claim 4.

29. A method of treating a bacterial infection in a mammal comprising administering to the mammal an antibacterial amount of a compound of claim 5.

30. A method of treating a bacterial infection in a mammal comprising administering to the mammal an antibacterial amount of a compound of claim 6.

31. A method of treating a bacterial infection in a mammal comprising administering to the mammal an antibacterial amount of a compound of claim 7.

32. A method of treating a bacterial infection in a mammal comprising administering to the mammal an antibacterial amount of a compound of claim 8.

33. A method of treating a bacterial infection in a mammal comprising administering to the mammal an antibacterial amount of a compound of claim 9.

34. A method of treating a bacterial infection in a mammal comprising administering to the mammal an antibacterial amount of the compound of claim 10.

35. A method of treating a bacterial infection in a mammal comprising administering to the mammal an antibacterial amount of the compound of claim 11.

36. A method of treating a bacterial infection in a mammal comprising administering to the mammal an antibacterial amount of the compound of claim 12.

* * * * *